(12) United States Patent
Liang et al.

(10) Patent No.: US 10,336,689 B1
(45) Date of Patent: Jul. 2, 2019

(54) GOSSYPOL EFLORNITHINE SCHIFF BASE COMPOUND WITH ANTITUMOR ACTIVITIES AND A METHOD OF PREPARING THE SAME

(71) Applicants: Chengyuan Liang, Xi'an (CN); Shunjun Ding, Xi'an (CN); Nan Hui, Xi'an (CN); Juan Li, Xi'an (CN); Dezhu Zhang, Xi'an (CN); Xiaolin Xie, Xi'an (CN)

(72) Inventors: Chengyuan Liang, Xi'an (CN); Shunjun Ding, Xi'an (CN); Nan Hui, Xi'an (CN); Juan Li, Xi'an (CN); Dezhu Zhang, Xi'an (CN); Xiaolin Xie, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/359,963

(22) Filed: Mar. 20, 2019

(30) Foreign Application Priority Data

Mar. 10, 2019 (CN) .......................... 2019 1 0177773

(51) Int. Cl.
  *C07C 251/24* (2006.01)
  *A61P 35/00* (2006.01)
  *C07C 249/02* (2006.01)

(52) U.S. Cl.
  CPC ............ *C07C 251/24* (2013.01); *A61P 35/00* (2018.01); *C07C 249/02* (2013.01)

(58) Field of Classification Search
  CPC ..... C07C 251/24; C07C 249/02; C07C 45/00; C07C 45/516; C07C 45/79; C07C 51/493; A61K 31/192; A61P 35/00
  See application file for complete search history.

(56) References Cited

U.S. PATENT DOCUMENTS 7,557,251 B2 * 7/2009 Wang .................... A61K 31/192
  562/607
2009/0010878 A1 * 1/2009 Holmlund .............. A61K 31/11
  424/85.2

* cited by examiner

*Primary Examiner* — Jafar F Parsa

(57) ABSTRACT

A gossypol eflornithine Schiff base compound having the following Formula I:

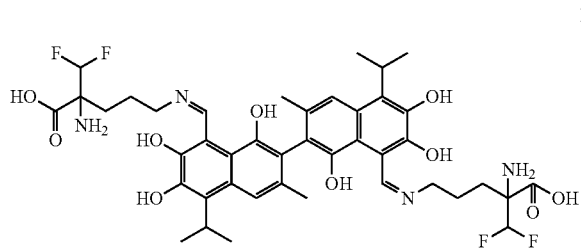

is disclosed. A method of preparing the compound of Formula I is also disclosed.

7 Claims, No Drawings

GOSSYPOL EFLORNITHINE SCHIFF BASE COMPOUND WITH ANTITUMOR ACTIVITIES AND A METHOD OF PREPARING THE SAME

The present invention claims priority to Chinese Patent Application No.: 201910177773.X, Filed on Mar. 10, 2019, which is incorporated by reference for all purposes as if fully set forth herein.

BACKGROUND OF THE INVENTION

Field of the Invention

The present invention relates to the field of pharmaceutical chemistry, and in particular to a gossypol eflornithine Schiff base compound with antitumor activities and a method of preparing the same.

Discussion of the Related Art

Gossypol (compound of formula II) is a polyphenolic bis-naphthalene aldehyde compound, and a natural yellow pigment found in small cell glands between cotton cells. It is an inhibitor of the anti-apoptotic protein of the Bcl-2 family, not only effectively blocking the binding pocket of Bcl-2, Bcl.-xL and BH3, but also blockers binding to Mcl-1 (a homologous protein of Bcl-2).

Eflornithine (compound of formula III), an ornithine decarboxylase inhibitor, can significantly inhibit the proliferation of rat colon cancer cells caused by demethylation and inhibit the growth of colon tumor cells in mice. It has anti-tumor effects, and can be used to treat *Pneumocystis carinii* pneumonia and trypanosomiasis.

Schiff base compounds have unique structural characteristics, i.e., a N-atom with a lone pair of electrons. They have good pairing ability, and can react with various types of groups to obtain various derivatives. They have broad applications, specially in chemical and biological applications.

The inventors designed and synthesized a gossypol eflornithine Schiff base compound with gossypol and eflornithine as starting materials.

SUMMARY OF THE INVENTION

In one embodiment, the present invention provides a gossypol eflornithine Schiff base compound having the following Formula I:

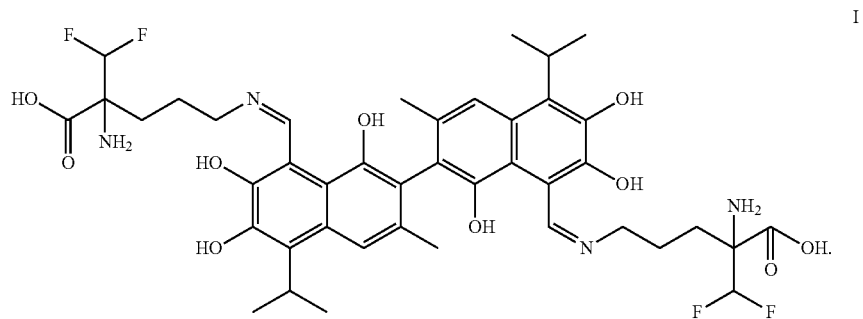 [SMILES: Cc1cc2c(C(C)C)c(O)c(O)c(/C=N\CCCC(N)(C(=O)O)C(F)F)c2c(O)c1-c1c(C)cc2c(C(C)C)c(O)c(O)c(/C=N\CCCC(N)(C(=O)O)C(F)F)c2c1O]

In another embodiment, the present invention provides a method of preparing the compound of Formula I of claim 1. The method includes:

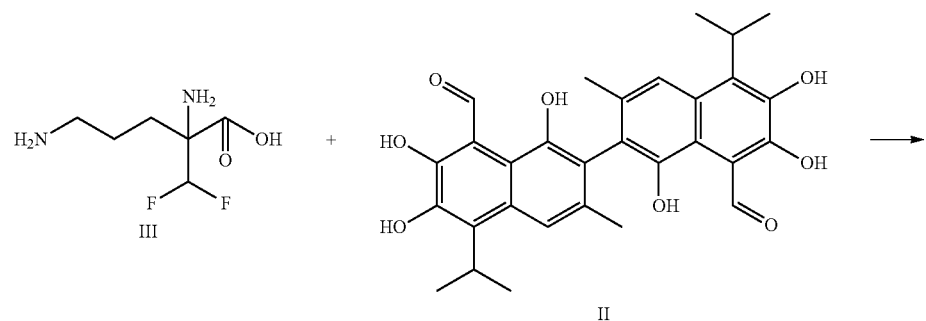

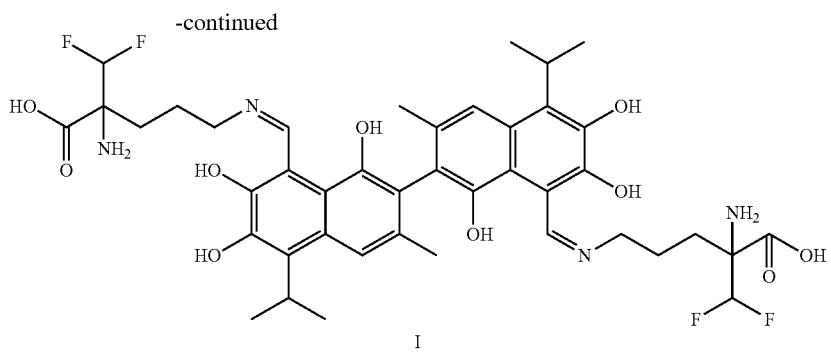

I (1) placing a compound of Formula III and a compound of Formula II, in a molar ratio of 2:1-3:1, and a solvent to a flask to form a mixture, adding a catalyst to the mixture, and stirring and heating the mixture at 60-80° C. for 1-3 hours;

(2) filtering the mixture and washing with the solvent to obtain a crude product of the compound of Formula I; and (3) recrystallizing the crude product of the compound of Formula I in the solvent to obtain the compound of Formula I.

In another embodiment, the solvent is selected from the group consisting of methanol, ethanol, toluene, and isopropanol.

In another embodiment, the catalyst is selected from the group consisting of acetic acid, tosylic acid, and ZnCl$_2$.

In another embodiment, the molar ratio of the compound of Formula III and the compound of Formula II is 2.5:1.

In another embodiment, the mixture was heated at 75° C.

In another embodiment, the mixture was heated for 2 hours.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

The present invention provides a gossypol eflornithine Schiff base compound having the following Formula I:

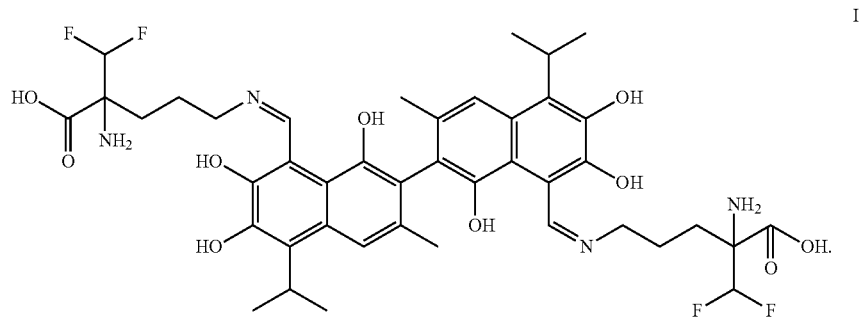 [SMILES: Cc1cc2c(C(C)C)c(O)c(O)c(/C=N\CCCC(N)(C(=O)O)C(F)F)c2c(O)c1-c1c(C)cc2c(C(C)C)c(O)c(O)c(/C=N\CCCC(N)(C(=O)O)C(F)F)c2c1O]

The present invention also provides a method of synthesizing the compound of Formula I. The synthetic route is as follows:

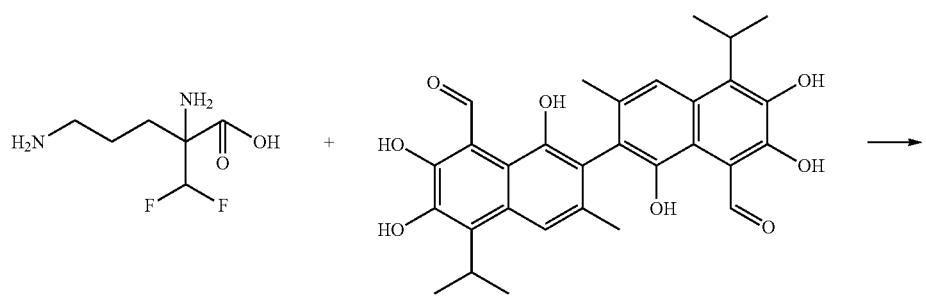

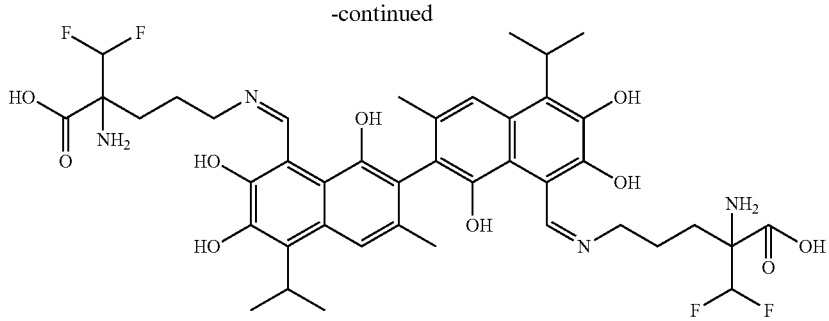

The synthesis of the compound of formula I includes the following steps.

(1) placing of eflornithine and gossypol, in a molar ratio of 2:1 to 3:1, and a solvent in a three-necked flask to form a mixture, adding a catalyst to the mixture, and stirring and heating the mixture at 60-80° C. for 1-3 hours to synthesize the gossypol eflornithine Schiff base compound;

(2) filtering the mixture and washing with the solvent to obtain a crude product of the gossypol eflornithine Schiff base compound; and (3) recrystallizing the crude product of gossypol eflornithine Schiff base compound in the solvent to obtain purified gossypol eflornithine Schiff base compound.

In the above steps (1), (2), and (3), the solvent is preferably ethanol.

In the above step (1), the catalyst is preferably acetic acid.

In the above step (1), the molar ratio of eflornithine and gossypol is preferably 2.5:1.

In the above step (1), the mixture was heated at 75° C.

In the above step (1), the mixture was heated for 2 hours.

Advantages of the present invention are: the inventors use gossypol as a key starting material, and combine gossypol with eflornithine to synthesize a gossypol eflornithine Schiff base compound with high bioavailability. The synthetic route is environmentally friendly, and has low production cost, high operation safety, and few reaction steps. The starting raw are fully utilized. The synthetic method is suitable for industrial production.

Example 1: Preparing the Gossypol Eflornithine Schiff Base Compound

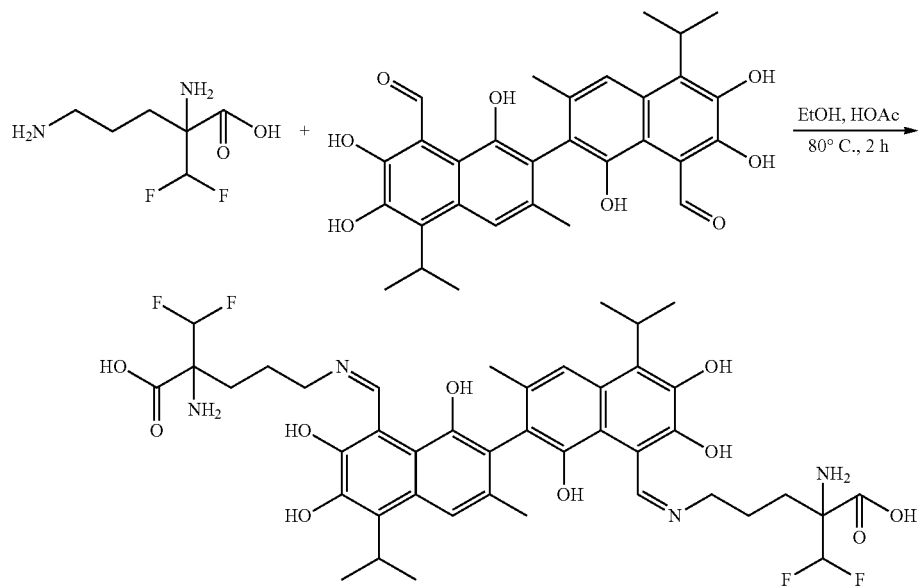

1.82 gram of gossypol (10 mmol), 2.07 grams of eflornithine (4 mmol), and 50 mL anhydrous ethanol were added to a 100 mL three-necked flask. 3 drops of acetic acid was added to the mixture. The mixture was then heated in water bath to 80° C. for 2 hours. The mixture was cooled to room temperature, and filtered and washed with anhydrous ethanol three times to obtain a crude product. The crude product was recrystallized in anhydrous ethanol to obtain 2.16 grams of the compound of Formula I, a yield of 63.73%.

Brown crystalline powder, M.P.: 232.8° C. $^1$H-NMR (400 MHz, DMSO-d6) δ (ppm): 12.35 (2H, s), 9.44 (1H, s), 9.01 (1H, s), 8.12 (2H, s), 6.13 (2H, s), 5.88 (6H, s), 5.60 (4H, s), 4.07 (4H, t), 3.53 (2H, m), 2.90 (6H, s), 1.74 (4H, t), 1.63 (4H, m), 1.29 (12H, d); $^{13}$C-NMR (100 MHz, DMSO-d6) δ (ppm): 178.8, 160.8, 153.4, 146.1, 144.1, 132.5, 130.7, 128.7, 119.0, 117.4, 112.2, 107.5, 70.5, 55.8, 27.4, 27.1, 24.0, 23.4, 16.4; MS (ESI) for (M+H)$^+$: 847.4.

Example 2: Preparing the Gossypol Eflornithine Schiff Base Compound

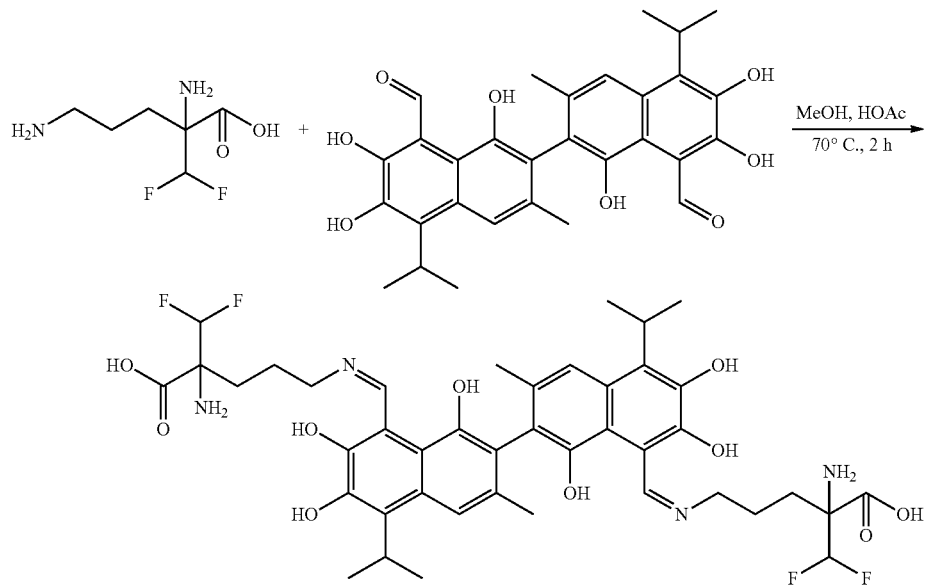

1.46 gram of gossypol (8 mmol), 2.07 grams of eflornithine (4 mmol), and 50 mL methanol were added to a 100 mL three-necked flask. 3 drops of acetic acid was added to the mixture. The mixture was then heated in water bath to 70° C. for 2 hours. The mixture was cooled to room temperature, and filtered and washed with methanol three times to obtain a crude product. The crude product was recrystallized in methanol to obtain 1.76 grams of the compound of Formula I, a yield of 51.97%.

Example 3: Preparing the Gossypol Eflornithine Schiff Base Compound 1.82 gram of gossypol (10 mmol), 2.07 grams of eflornithine (4 mmol), and 50 mL toluene were added to a 100 mL three-necked flask. 3 drops of acetic acid was added to the mixture. The mixture was then heated in water bath to 70° C. for 1 hour. The mixture was cooled to room temperature, and filtered and washed with toluene three times to obtain a crude product. The crude product was recrystallized in toluene to obtain 0.86 gram of the compound of Formula I, a yield of 27.21%.

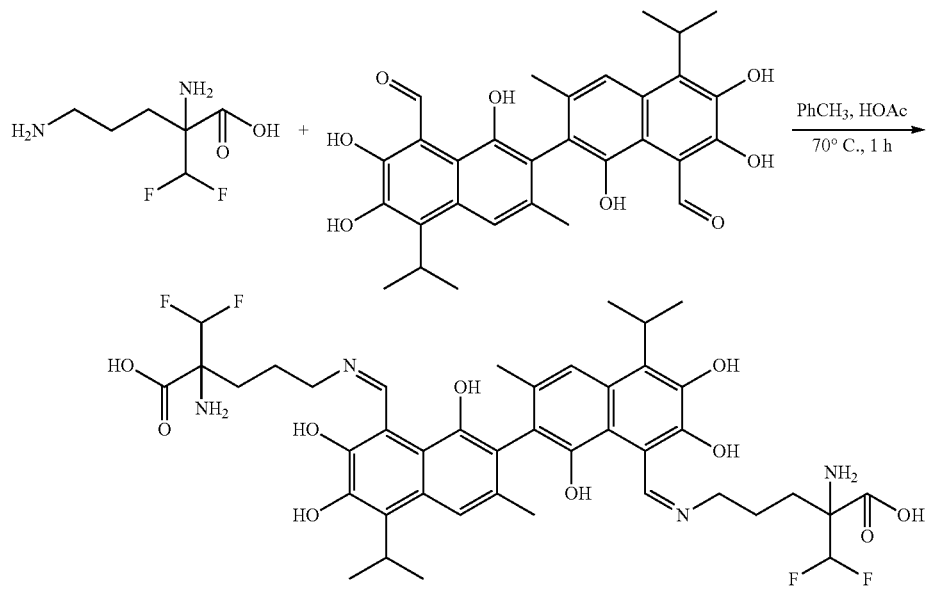

Example 4: Preparing the Gossypol Eflornithine Schiff Base Compound

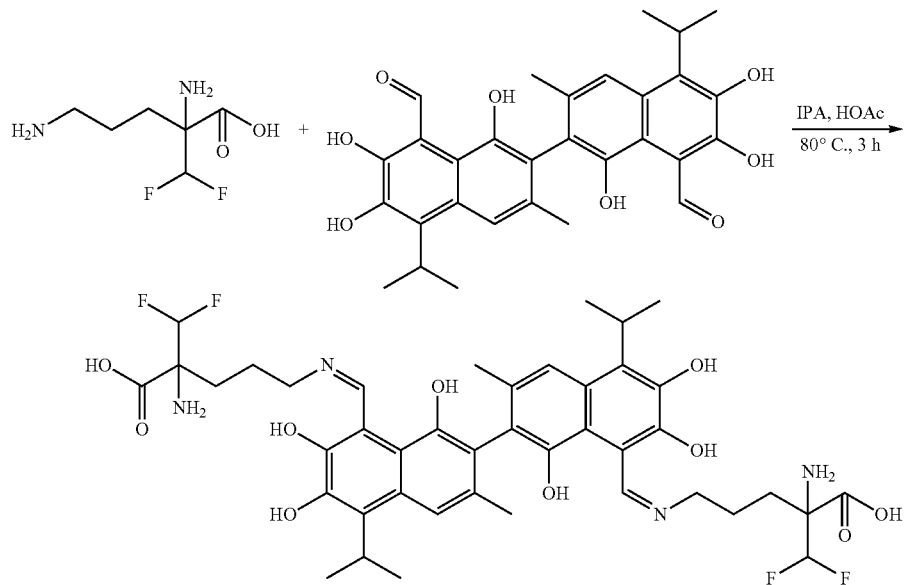

2.19 gram of gossypol (12 mmol), 2.07 grams of eflornithine (4 mmol), and 50 mL isopropanol (IPA) were added to a 100 mL three-necked flask. 3 drops of acetic acid was added to the mixture. The mixture was then heated in water bath to 80° C. for 3 hours. The mixture was cooled to room temperature, and filtered and washed with isopropanol three times to obtain a crude product. The crude product was recrystallized in isopropanol to obtain 2.06 grams of the compound of Formula I, a yield of 60.88%.

Example 5: Preparing the Gossypol Eflornithine Schiff Base Compound 1.82 gram of gossypol (10 mmol), 2.07 grams of eflornithine (4 mmol), and 50 mL anhydrous ethanol were added to a 100 mL three-necked flask. 0.17 gram of tosylic acid (TsOH) was added to the mixture. The mixture was then heated in water bath to 60° C. for 1 hour. The mixture was cooled to room temperature, and filtered and washed with anhydrous ethanol three times to obtain a crude product. The crude product was recrystallized in anhydrous ethanol to obtain 0.99 gram of the compound of Formula I, a yield of 37.54%.

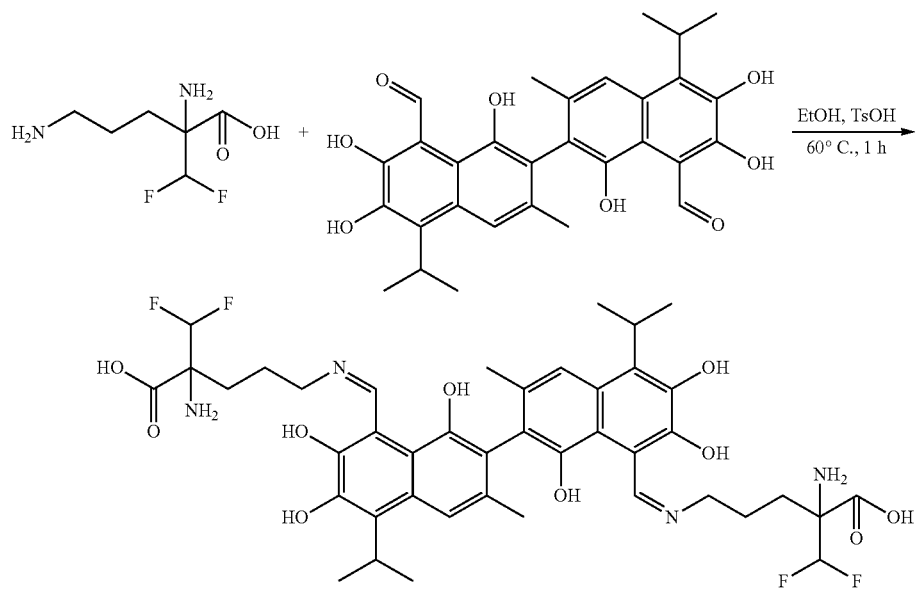

Example 6: Preparing the Gossypol Eflornithine Schiff Base Compound

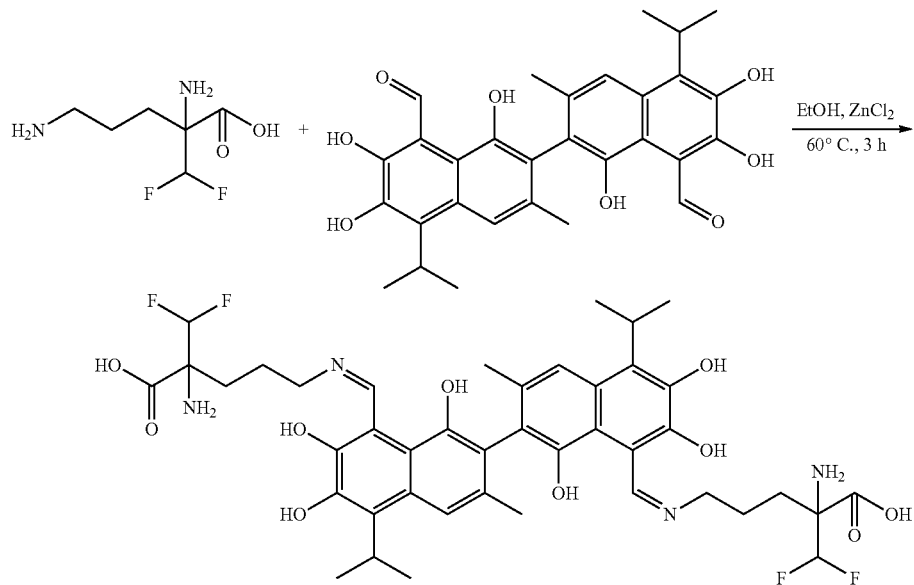

1.46 gram of gossypol (8 mmol), 2.07 grams of eflornithine (4 mmol), and 50 mL anhydrous ethanol were added to a 100 mL three-necked flask. 0.13 gram of $ZnCl_2$ was added to the mixture. The mixture was then heated in water bath to 60° C. for 3 hours. The mixture was cooled to room temperature, and filtered and washed with anhydrous ethanol three times to obtain a crude product. The crude product was recrystallized in anhydrous ethanol to obtain 1.65 grams of the compound of Formula I, a yield of 49.08%.

Example 7: Preparing the Gossypol Eflornithine Schiff Base Compound 1.82 gram of gossypol (10 mmol), 2.07 grams of eflornithine (4 mmol), and 50 mL methanol were added to a 100 mL three-necked flask. 0.17 gram of tosylic acid (TsOH) was added to the mixture. The mixture was then heated in water bath to 80° C. for 1 hour. The mixture was cooled to room temperature, and filtered and washed with methanol three times to obtain a crude product. The crude product was recrystallized in methanol to obtain 1.92 gram of the compound of Formula I, a yield of 56.70%.

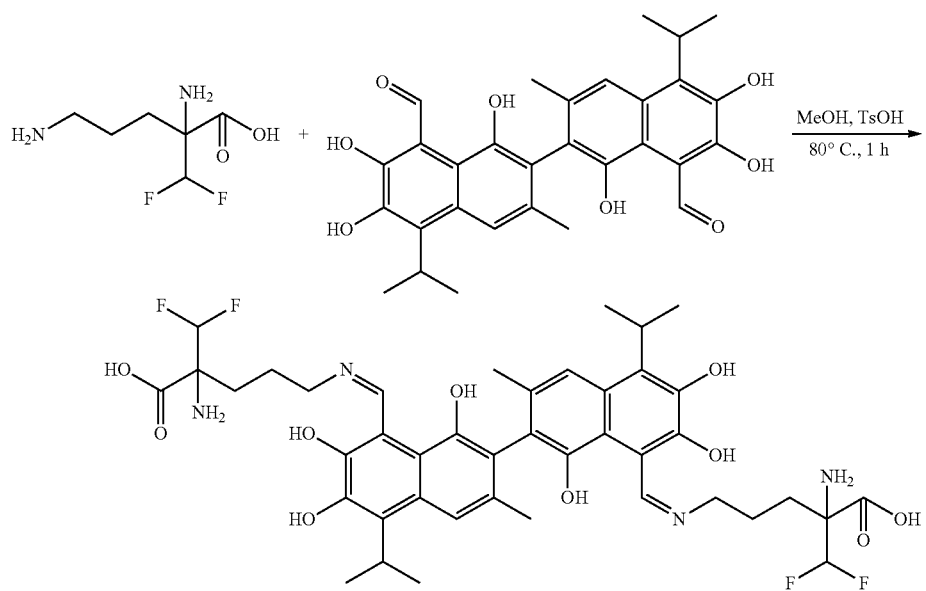

Example 8: Preparing the Gossypol Eflornithine Schiff Base Compound

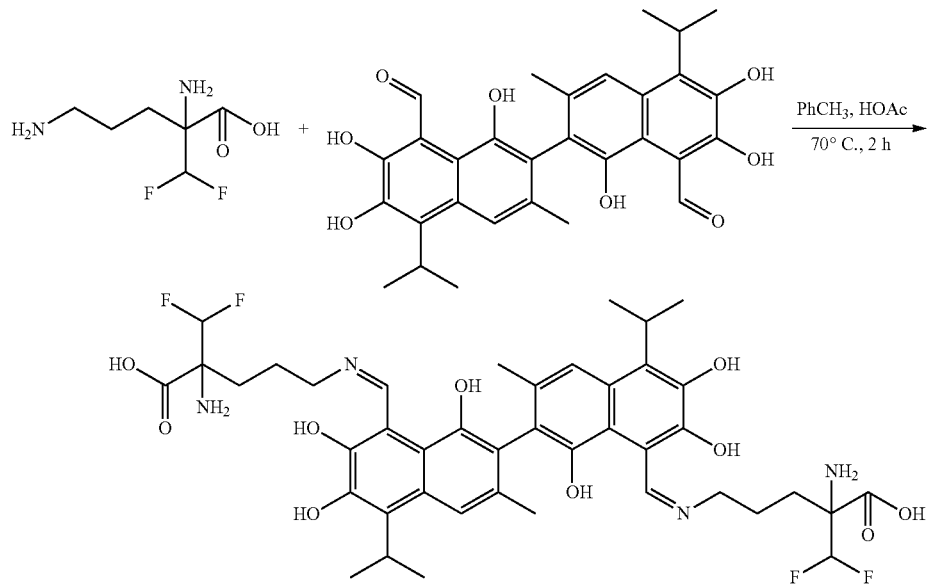

2.19 gram of gossypol (12 mmol), 2.07 grams of eflornithine (4 mmol), and 50 mL toluene were added to a 100 mL three-necked flask. 3 drops of acetic acid was added to the mixture. The mixture was then heated in water bath to 70° C. for 2 hours. The mixture was cooled to room temperature, and filtered and washed with toluene three times to obtain a crude product. The crude product was recrystallized in toluene to obtain 1.74 gram of the compound of Formula I, a yield of 51.36%.

Example 9: Preparing the Gossypol Eflornithine Schiff Base Compound 1.46 gram of gossypol (8 mmol), 2.07 grams of eflornithine (4 mmol), and 50 mL isopropanol (IPA) were added to a 100 mL three-necked flask. 0.13 gram of $ZnCl_2$ (1 mmol) was added to the mixture. The mixture was then heated in water bath to 80° C. for 2 hours. The mixture was cooled to room temperature, and filtered and washed with isopropanol three times to obtain a crude product. The crude product was recrystallized in isopropanol to obtain 21.88 grams of the compound of Formula I, a yield of 55.67%.

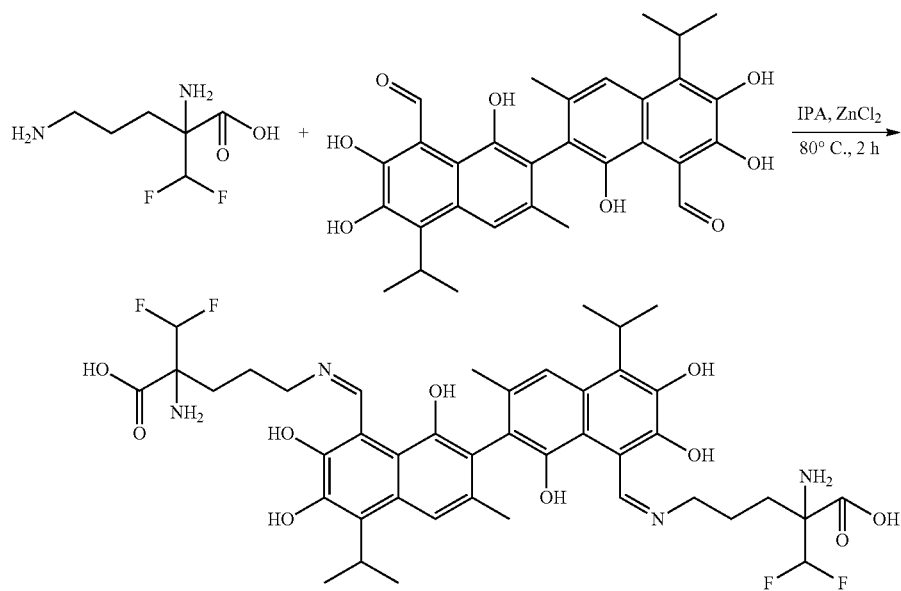

Example 10: Preparing the Gossypol Eflornithine Schiff Base Compound

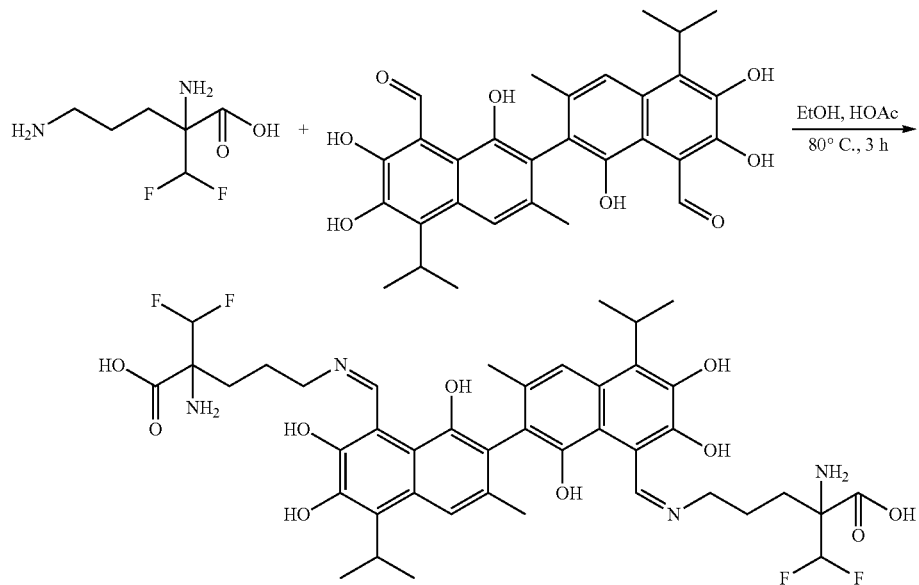

2.19 gram of gossypol (12 mmol), 2.07 grams of eflornithine (4 mmol), and 50 mL anhydrous ethanol were added to a 100 mL three-necked flask. 3 drops of acetic acid was added to the mixture. The mixture was then heated in water bath to 80° C. for 3 hours. The mixture was cooled to room temperature, and filtered and washed with anhydrous ethanol three times to obtain a crude product. The crude product was recrystallized in anhydrous ethanol to obtain 2.08 grams of the compound of Formula I, a yield of 61.31%.

Example 11: Preparing the Gossypol Eflornithine Schiff Base Compound 1.46 gram of gossypol (8 mmol), 2.07 grams of eflornithine (4 mmol), and 50 mL methanol were added to a 100 mL three-necked flask. 0.17 gram of tosylic acid (TsOH) was added to the mixture. The mixture was then heated in water bath to 80° C. for 2 hours. The mixture was cooled to room temperature, and filtered and washed with methanol three times to obtain a crude product. The crude product was recrystallized in methanol to obtain 1.85 gram of the compound of Formula I, a yield of 54.62%.

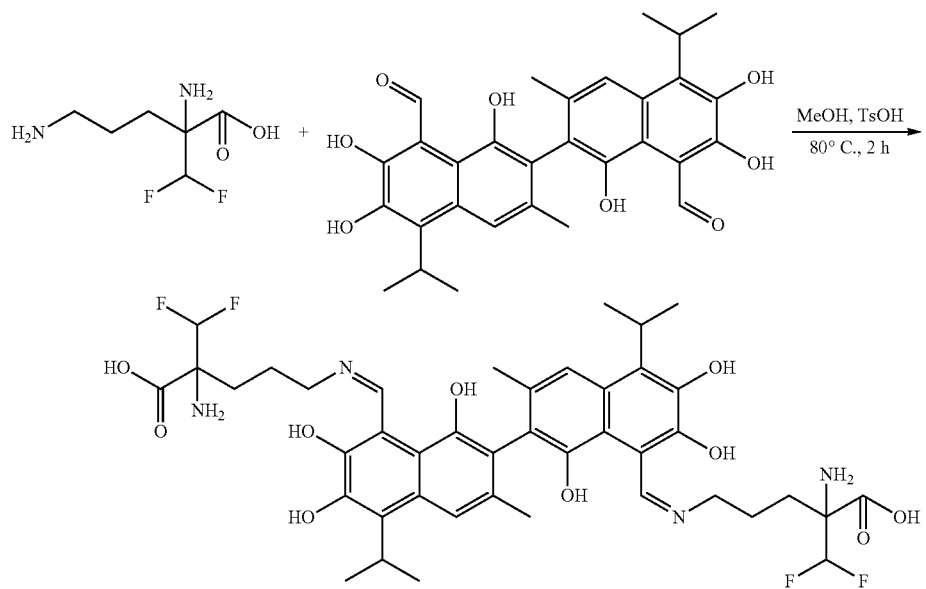

Example 12: Preparing the Gossypol Eflornithine Schiff Base Compound

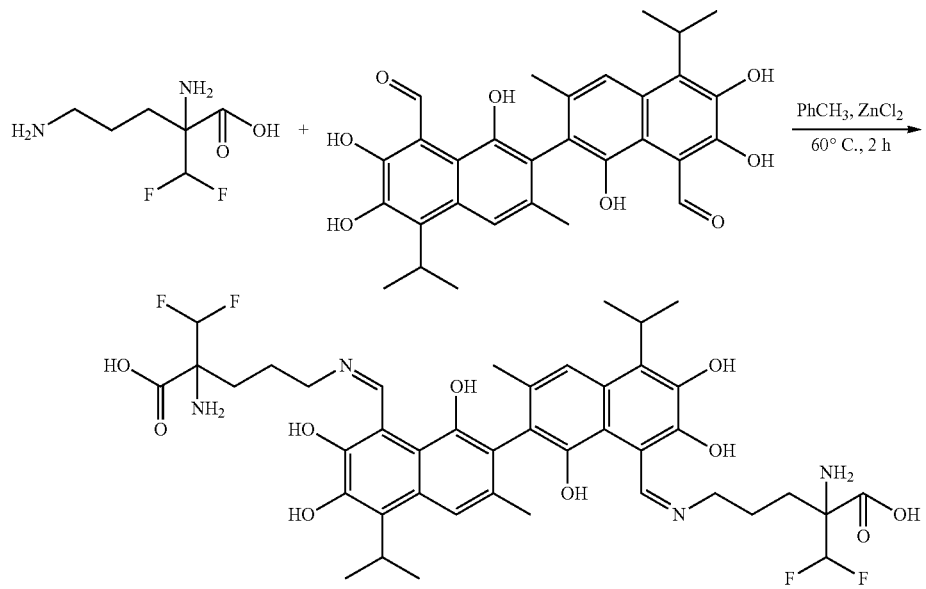

1.82 gram of gossypol (10 mmol), 2.07 grams of eflornithine (4 mmol), and 50 mL toluene were added to a 100 mL three-necked flask. 0.13 gram of $ZnCl_2$ (1 mmol) was added to the mixture. The mixture was then heated in water bath to 60° C. for 2 hours. The mixture was cooled to room temperature, and filtered and washed with toluene three times to obtain a crude product. The crude product was recrystallized in toluene to obtain 2.00 gram of the compound of Formula I, a yield of 58.98%.

Example 13: The Anti-Tumor Activity Test of the Gossypol Eflornithine Schiff Base Compound The gossypol eflornithine Schiff base compound was subjected to tumor cell proliferation inhibition test, and conventional MTT method was used.

Cell lines: human hepatoma cells (HepG2), human lung cancer cells (A-549), human gastric cancer cells (SGC-7901). The culture medium was DMEM+15% NBS+double antibody.

Sample solution preparation: after dissolving with DMSO (Merck), PBS (−) was added to obtain 100 μmol/L solution or homogeneous suspension. The solution was diluted with PBS (−) in DMSO to a final concentration of 0.1, 1, 10, 20, 40, 60, 80, 100 μmol/L.

Gossypol and eflornithine used as control solution, prepared under the same condition.

Cell culture: adherent growth Tumor cells were cultured in 1640 medium containing 10% inactivated neonatal bovine serum and penicillin, streptomycin (1 million U/L), placed in carbon dioxide incubator at 37° C., 5% $CO_2$, and saturated humidity. Cells were treated serially passaged 2-3 times. The first culture was washed with PBS 2 times, and digested with trypsin. Fresh culture medium was added evenly, cells were adjusted to an appropriate concentration and transferred into a new culture flask. Cell in an exponential phase were chosen for the tests.

MTT Assay for Cell Viability and $IC_{50}$ Determination:

Experimental Principle: Living cells mitochondria in the dehydrogenase can reduce yellow MTT to water-insoluble blue-violet product MT (MTT formazan), deposited in the cells. The amount of production is proportional to the number of living cells. Dead cells do not reduce yellow MTT. DMSO can dissolve blue violet crystals, and the color depth is proportional to the amount contained, so the absorbance measured by the microplate reader can reflect the cell viability.

Methods: The exponential phase cells were digested and counted and seeded in 96-well plates at a density of 2×104/mL at 100 μl per well. After 24 hours of incubation, the cells to be tested were treated with 0.1, 1, 10, 20, 40, 60, 80, 100 μmol/L of the compounds. Each experimental group had 5 wells in each concentration, and the culture medium containing 0.4% DMSO was used as control. After 48 hours, the supernatant was discarded, and 100 μl of MTT ((2-(4,5-dimethyl-2-thiazolyl)-3,5-diphenyl-2H-tetrazole hydrobromide) (1 mg/mL) was added to each well. After another 4 hours, the supernatant was discarded, and 100 μl of DMSO was added to each well. After mixing, the absorbance was measured at 570 nm using a microplate reader. An $IC_{50}$ calculation software was used to determine the half inhibitory concentration ($IC_{50}$).

The test results are shown in Table 1. The compounds listed in the table correspond to the compounds described above.

TABLE 1

Half Inhibitory Concentration of Compounds on Different Tumor Cells $IC_{50}$ (unit: μmol/L)

| Compounds | $IC_{50}$ (μmol/L) | | |
|---|---|---|---|
| | HepG2 | A549 | SGC-7901 |
| Gossypol eflornithine Schiff base compound | 20.06 ± 0.57 | 11.63 ± 0.20 | 11.08 ± 0.34 |
| Gossypol | 9.55 ± 0.41 | 12.96 ± 0.32 | 19.81 ± 0.66 |
| Eflornithine | >100 | >100 | >100 |

The results show that the gossypol eflornithine Schiff base compound has good antitumor activities in the three cell lines tested. Specifically, the gossypol eflornithine Schiff base compound has better antitumor activity against SGC-7901 cell lines than gossypol. The above experimental results indicate that the gossypol eflornithine Schiff base compound of the present invention has good antitumor activities and can be used for the study of antitumor agents.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A gossypol eflornithine Schiff base compound having the following Formula I:

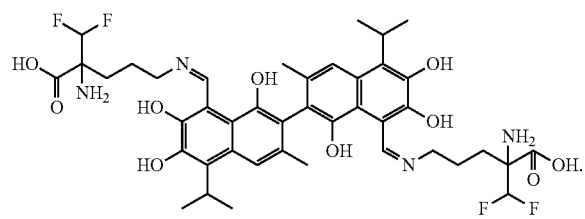

I

2. A method of preparing the compound of Formula I of claim 1, comprising:

(1) placing a compound of Formula III and a compound of Formula II, in a molar ratio of 2:1-3:1, and a solvent to a flask to form a mixture, adding a catalyst to the mixture, and stirring and heating the mixture at 60-80° C. for 1-3 hours;

(2) filtering the mixture and washing with the solvent to obtain a crude product of the compound of Formula I; and (3) recrystallizing the crude product of the compound of Formula I in the solvent to obtain the compound of Formula I.

3. The method of claim 2, wherein the solvent is selected from the group consisting of methanol, ethanol, toluene, and isopropanol.

4. The method of claim 2, wherein the catalyst is selected from the group consisting of acetic acid, tosylic acid, and $ZnCl_2$.

5. The method of claim 2, wherein the molar ratio of the compound of Formula III and the compound of Formula II is 2.5:1.

6. The method of claim 2, wherein the mixture was heated at 75° C.

7. The method of claim 2, wherein the mixture was heated for 2 hours.

* * * * *

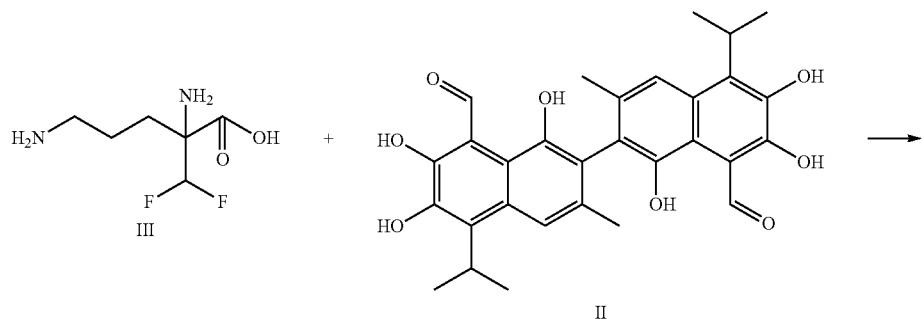

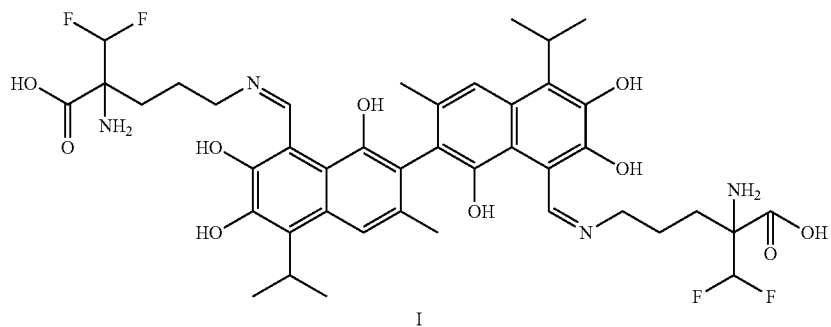

I